United States Patent
Klatzmann et al.

(10) Patent No.: US 7,074,411 B1
(45) Date of Patent: Jul. 11, 2006

(54) α-β C4BP-TYPE RECOMBINANT HETEROMULTIMERIC PROTEINS

(75) Inventors: David Klatzmann, Paris (FR); Jacques Cohen, Reims (FR)

(73) Assignees: Universite Pierre et Marie Curie (Paris VI), Paris (FR); Universite de Reims Champagne-Ardennes, Reims (FR)

( * ) Notice: Subject to any disclaimer, the term of this patent is extended or adjusted under 35 U.S.C. 154(b) by 0 days.

(21) Appl. No.: 08/983,474

(22) PCT Filed: Jul. 18, 1996

(86) PCT No.: PCT/FR96/01132

§ 371 (c)(1),
(2), (4) Date: Jun. 30, 1998

(87) PCT Pub. No.: WO97/04109

PCT Pub. Date: Feb. 6, 1997

(30) Foreign Application Priority Data

Jul. 21, 1995 (FR) .................................... 95 08901

(51) Int. Cl.
| | |
|---|---|
| *A61K 38/17* | (2006.01) |
| *C12N 5/10* | (2006.01) |
| *C12N 15/63* | (2006.01) |
| *C07K 14/47* | (2006.01) |

(52) U.S. Cl. .................. 424/192.1; 530/350; 435/69.7; 435/71.1; 435/71.2; 435/325; 435/320.1; 435/810

(58) Field of Classification Search .............. 435/69.7, 435/69.1, 172.3, 325, 320.1; 514/2; 530/301, 530/350; 424/192.1
See application file for complete search history.

(56) References Cited

U.S. PATENT DOCUMENTS

| | | | | |
|---|---|---|---|---|
| 5,405,946 A | * | 4/1995 | Griffin et al. ................ | 530/380 |
| 5,679,546 A | * | 10/1997 | Ko et al. .................... | 435/69.2 |
| 5,851,528 A | * | 12/1998 | Ko et al. .................. | 424/185.1 |

OTHER PUBLICATIONS

Haynes, B. F. et al., Update on Issues of HIV Vaccine Development, The Finnish Medical Society DUODECIM, Ann Med', vol. 28, pp. 39-41 Med, 1996.*
Fahey, J. L. et al., Status of Immune-based Therapies in HIV Infection and AIDS, Clin. Exp. Immunol., vol. 88, pp. 1-5, 1992.*
Rudinger, J et al., Peptide Hormones, ed. J. A. Parsons, University Park Press, Baltimore, pp. 1-7, 1976.*
Hillarp et al., Proc Natl Acad Sci 1990, vol. 87(3): pp. 1183-1187, esp. p. 1186: Figure 6.*
Horst Ibelgaufts, Dictionary of Cytokines 1995, VCH Publishers, Inc., New York, NY, esp. pp. 123 and 126.*
Anderson et al., J. Biol. Chem., "High affinity binding of human vitamin K-dependent protein S to a truncated recombinant beta-chain of C4b-binding protein expressed in *Escherichia coli*", Feb. 1993, 268, (5) P3033-6.
WO, A, 91 11461 (Biogen Inc.) Aug. 1991.
Morris, C., ed. *Dictionary of Science and Technology*, Academic Press, San Diego, Federal Register, Uniform Biological Material Transfer Agreement: Discussion of Public Comments Received; Publication of Final Format of the Agreement, Mar. 8, 1995, pp. 12771-12775.
Weir's Handbook of Experimental Immunology, 5th edition, *Cell Surface and Messenger Molecules of the Immune System*, Herzenberg, Stanford, CA, vol. II, Chapter 6, pp. 61.1-61.3, 61.13-61.14, 61.24-61.25.
*The Leucocyte Antigen Facts Book*, 2nd edition, Barclay et al., eds., Academic Press, San Diego, CA, pp. 2-17.

* cited by examiner

*Primary Examiner*—Prema Mertz
(74) *Attorney, Agent, or Firm*—Venable LLP; Michael A. Gollin; Nancy J. Axelrod

(57) ABSTRACT

A recombinant heteromultimeric protein including at least (a) a polypeptide fusion molecule A consisting of a C4BP α-chain C-terminal fragment and a polypeptide fragment heterologous to said α-chain, and (a) a polypeptide fusion molecule B consisting of a C4BP β-chain C-terminal fragment and a polypeptide fragment heterologous to said β-chain, wherein (a) and (b) are linked in the C-terminal portion to form said multimeric protein.

24 Claims, 6 Drawing Sheets

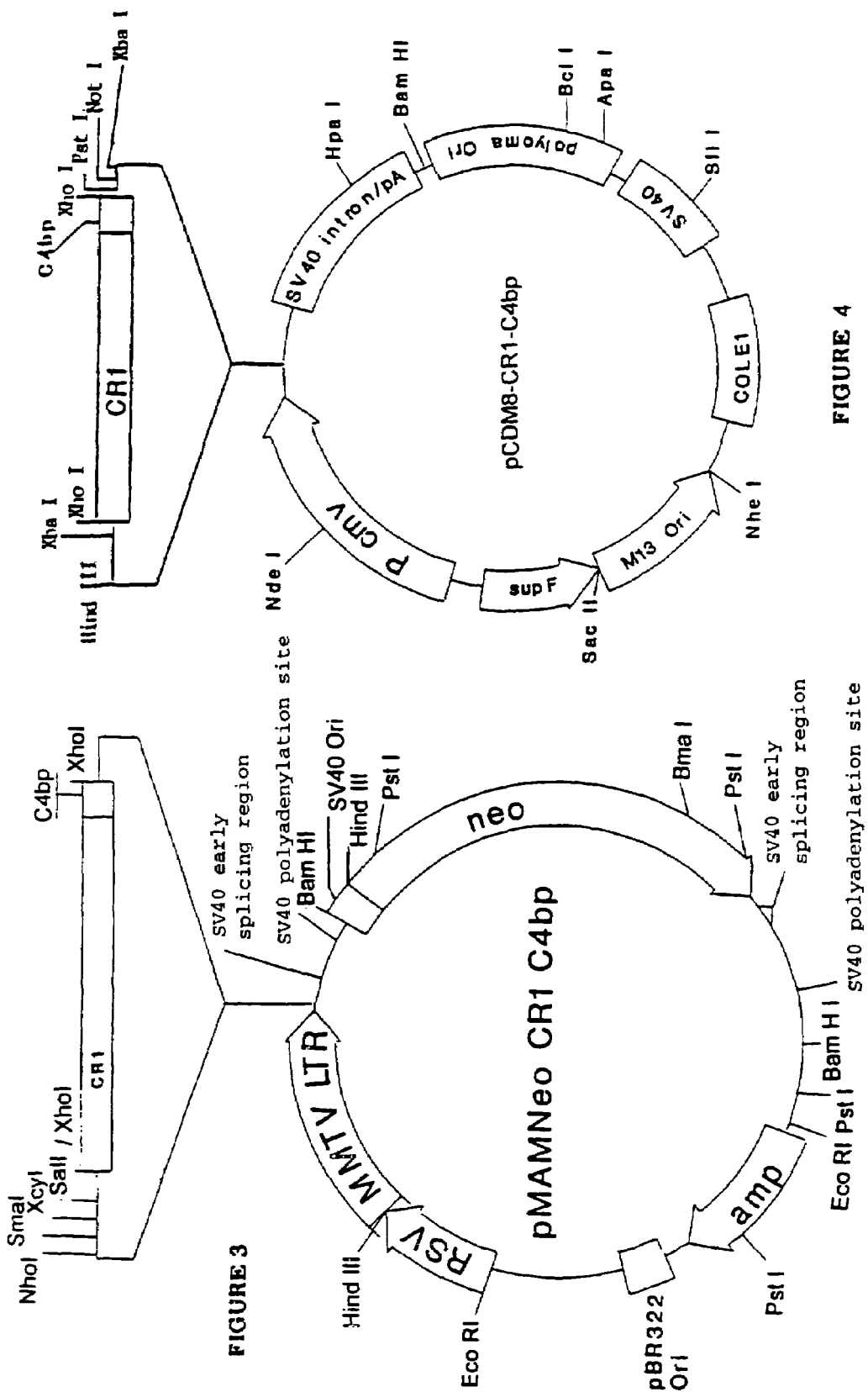

A B C D

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO: 1:

GAGACCCCCG AAGGCTGTGA                                                   20

(2) INFORMATION FOR SEQ ID NO: 2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO: 2:

CTCGAGTTAT AGTTCTTTAT CCCAAGTGG                                         29

(2) INFORMATION FOR SEQ ID NO: 3:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO: 3:

GCGGCCGCAG AGACCCCCGA AGGCTGTG                                                28

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 4:

CCACTTTGGA TAAAGAACTA TAA                                                    23

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 5:

ATTTCTAGAG AGTTATAGTT CTTTATCCAA AGTGGA                                      36

(2) INFORMATION FOR SEQ ID NO: 6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 6:

CCGGGACAGG TCCTGCTGGA ATCCAACATC AAGGTTCTGC CCACAG                           46

(2) INFORMATION FOR SEQ ID NO: 7:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Ser Thr Leu Asp Lys Glu Leu
        50                  55

(2) INFORMATION FOR SEQ ID NO: 8:

(i) SEQUENCE CHARACTERISTICS:
    (A) LENGTH: 57 amino acids
    (B) TYPE: amino acid
    (C) STRANDEDNESS: <Unknown>
    (D) TOPOLOGY: linear (ii) MOLECULE TYPE: peptide (xi) SEQUENCE DESCRIPTION: SEQ ID NO: 8:

Glu Ala Pro Lys Pro Glu Cys Glu Lys Ala Leu Leu Ala Phe Gln Glu
1               5                  10                  15
Ser Lys Asn Leu Cys Glu Ala Met Glu Asn Phe Met Gln Gln Leu Lys
            20                  25                  30
Glu Ser Gly Met Thr Met Glu Glu Leu Lys Tyr Ser Leu Glu Leu Lys
        35                  40                  45
Lys Ala Glu Leu Lys Ala Lys Leu Leu
50                  55

(2) INFORMATION FOR SEQ ID NO: 9:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Cys Leu Pro Asn Pro Glu Asp Val Lys Met Ala Leu Glu Val Tyr Lys
1               5                  10                  15
Leu Ser Leu Glu Ile Glu Gln Leu Glu Leu Gln Arg Asp Ser Ala Arg
            20                  25                  30
Gln Ser Thr Leu Asp Lys Glu Leu
        35                  40

(2) INFORMATION FOR SEQ ID NO: 10:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

Cys Glu Ala Met Glu Asn Phe Met Gln Gln Leu Lys Glu Ser Gly Met
1               5                  10                  15
Thr Met Glu Glu Leu Lys Tyr Ser Leu Glu Leu Lys Lys Ala Glu Leu
            20                  25                  30
Lys Ala Lys Leu Leu
        35

US 7,074,411 B1

α-β C4BP-TYPE RECOMBINANT HETEROMULTIMERIC PROTEINS

The present invention relates to hetero-multimeric fusion proteins of the C4BP type, to compositions which comprise them and to the process for preparing them. More specifically, this invention relates to heteromultimeric fusion proteins which are derived by combining α and β monomers of the C4BP protein, or fragments of these monomers, with these monomers being fused to polypeptides which are derived from functionally active proteins having ligand or receptor properties.

The numbers in brackets relate to the bibliographical list at the end of the text.

"C4BP-binding protein" (C4BP), previously termed proline-rich protein, is an important protein both in the coagulation system (1) and in the complement system (2, 3). The major form of C4BP consists of 7 identical α chains of 75 Kd and of one β chain of 45 Kd. The nucleotide sequence of the cDNA and the protein sequence of the α chain have been determined (4). A complete description of human C4BP, its isolation and its characterization have been given in (2); an update of knowledge regarding this molecule has been presented in summary form in (5).

Up until 1990, it was not known that the two chains, α and β, existed; it was only in 1990 that A. Hillarp demonstrated for the first time that a new subunit, which was designated the β chain, and which contains the site for binding to the S protein (6, 7), existed in the multimeric protein.

The BIOGEN Patent Application WO 91/1146 describes multimeric proteins of the C4BP type which consist solely of α monomers in which the N-terminal moiety has been replaced by a fragment of the CD4 protein.

However, the constructs which are described in this document only make use of the α chain, since the β chain was unknown at that time. The drawback of these constructs is that it is extremely difficult, on the one hand, to control the physical state of the synthetic molecule, that is the number of monomers which combine with each other, and, on the other hand, it is extremely difficult, when it is desired to combine two different functional moieties within the multimer, to control the proportions of these functional elements.

Therapeutic agents which function at the level of the immune system, whether the agent be a cellular or humoral agent, or an immunointervention agent, have developed in a large number of directions; however, the areas of application of therapeutic immunointerventions using antibodies, in particular monoclonal antibodies, currently remain modest due to the fact that the phenomena which take place after the antibodies have bound to the cell are poorly controlled. Thus, it is currently only known how to use these antibodies, even when humanized, for the purposes of cell destruction.

The development of bispecific antibodies has also been envisaged, with some of these antibodies comprising one moiety which is capable of binding to an antigen, with the other moiety having the role of a ligand in relation to a receptor, thereby making it possible to direct the antibody plus antigen toward a cell system (8). However, these systems do not enable several ligands to be combined in one and the same complex, which appears in some cases to be a prerequisite for triggering an immune response.

Another system which has been proposed for achieving multimers is based on the IgM Fc; this system suffers from several drawbacks: the main drawback is that of creating molecular species of varying size, leaving free sulfhydryl residues which are able to react with plasma molecules or cell surfaces. Furthermore, the cell receptor-binding and complement-activating functions of the Fc fragment may be undesirable.

By contrast, a recombinant heteromultimeric molecule can make it possible to combine several antibody functions, or several enzyme molecules or several antigens, or fragments or mixtures thereof, thereby creating a multivalent tracer which possesses a potential for amplifying the detected signal which is superior to that of a fusion protein which combines a single antibody or a bispecific antibody and an enzyme or antigen molecule.

This approach makes it possible to envisage, in addition to opsonization by means of triggering cellular immunity, the induced implementation of humoral immunity of activating complement.

SUMMARY OF THE INVENTION

The object of the present invention is therefore to develop recombinant soluble heteromultimeric chimeric molecules which combine different functions in one and the same molecule, with a view to achieving immunointervention in human immune pathologies. These molecules will make it possible to intervene in the physiopathological mechanisms of different ailments, in particular in the spheres relating to:

the pathology of the transport and elimination of immune complexes by the erythrocytes, with an application, in particular, to disseminated lupus erythematosus, or to HIV infections, the capture of antigens which is mediated by Fc receptors on the surface of the cells of the monocyte/macrophage cell line, modulation by molecules having soluble CD16 activity, the prevention of anti-erythrocyte Rh(D) alloimmunization, the inhibition of cell penetration by the HIV virus using soluble forms of CD4, antibodies which are directed against the constituents of the virus, and/or molecules having enzymic functions.

The present invention relates to a recombinant multimeric protein which is characterized in that it comprises at least:

a) a polypeptide fusion molecule A, which consists of a C-terminal fragment of the α chain of C4BP, contained between amino acids 549 and 124, and a polypeptide fragment which is heterologous in relation to said α chain, b) a polypeptide fusion molecule B, which consists of a C-terminal fragment of the β chain of C4BP, contained between amino acids 235 and 120, and a polypeptide fragment which is heterologous in relation to the β chain, with amino acids 549 or 235 representing the respective C-terminal ends of the fusion molecules and the heterologous fragments being fused by their C-terminal end to the residue of the α and β chains, respectively, and with the molecules in a) and b) being linked to each other by way of their C-terminal moiety in order to form said multimeric protein.

Preferably, a recombinant multimeric protein according to the invention is characterized in that the C-terminal fragment of the α chain is contained between amino acids 549 and 493, and in that the C-terminal fragment of the β chain is contained between amino acids 235 and 176. The fusion molecules are reassociated by forming disulfide bridges between the cysteines in positions 498 and 510 of the C-terminal end of the α chain and the cysteines in positions 199 and 185 of the C-terminal end of the β chain.

Any chimera between the α and β chains which links, where appropriate, a cysteine of the α chain and a cysteine of the β chain in the A or B fusion molecule, or in the two fusion molecules, is also included in the scope of the constructs of the multimeric proteins of the invention.

In particular, the possibility of altering the spacing between the two cysteines can enable the number of monomers which are included in the constitution of the multimer to be altered.

By way of illustration, an increase in the distance between the cysteines can lead to an increase in the number of monomers which are included in the multimer; on the other hand, a decrease in this distance would result in a decrease in this number. In certain cases, it can be advantageous to alter this distance so as to alter the controlled reassociation of the two types of chain carrying a ligand or a receptor, both with regard to the number of chains and their proportions.

In the present invention, a multimerizing system has been developed which makes it possible to obtain heptameric and octameric formulae using the C-terminal ends of the basic chains of the C4BP molecule. Multimerization of molecules whose C-terminal ends have been replaced by the C4BP α C-terminal moiety or the C4BP β C-terminal moiety produces an octameric form.

Whatever the case, the fragment which is derived from the β chain of C4BP should lack the sites for attachment to the S protein, which sites are located in the two SCRs of the proximal moiety of the N-terminal end of the β chain.

Thus, a recombinant multimeric protein according to the invention is characterized in that the ratio of the number of monomers α/β varies between 7/1 and 5/3 and is preferably 7/1 when the fragments of the C-terminal moieties have a homogeneous origin in fragments A and B above.

Ideally, the multimeric recombinant molecule is a protein which only combines human constituents, thereby avoiding any xenogenic immunization and not activating complement apart from specific functions which are intentionally added in this sense. Such a molecule should not interact with cell receptors or plasma molecules, and should thereby ensure that the activity of the chimeric molecule is improved due to its multivalence and that the life span of the molecule is extended.

A multimeric protein according to the present invention exhibits properties relating to immuno-intervention, in particular an ability to modulate the activity of complement with the aim of generating opsonization artificially. This result is obtained as a consequence of the heterofunctional character which can be attributed to this protein as a result of the contribution made by the heterologous N-terminal fragments.

To this end, a recombinant protein according to the invention is characterized in that the heterologous fragments in A and in B are derived from specific ligands of the immune system, in particular from lymphocyte surface proteins of the CD type, from antibodies or antibody fragments, or from antigens or antigen fragments; the heterologous fragments in A and B can be selected, depending on the application which is desired for the recombinant protein, and without this list being exhaustive, from the following polypeptides having a ligand activity:

i)—fragments derived from lymphocyte proteins are CD4, CD8, CD16 and CD35 (or CR1), ii)—antibodies or antibody fragments having an anti-erythrocyte specificity, in particular an anti-Rh(D) specificity, iii)—antigens, in particular vaccinating antigens such as the pre-S2 of hepatitis B virus, iv)—an enzyme which is intended for therapeutic purposes or, more specifically, the fragment of this enzyme which corresponds to the active site of said enzyme, which fragment can be fused to the C-terminal moiety of the alpha chain in order to form the A fragment, with it then being possible for the B fragment to consist of any type of polypeptide such as cited in i) to iii).

Even more particularly, combinations of A and B which are particularly advantageous for implementing the immunointervention of the invention can be multimeric proteins in which the polypeptide fusion fragments contain:

v)—in A, CD4 or a derivative of CD4, and in B, the sc Fv of an anti-Rh(D) antibody, or of other antibodies, in particular neutralizing antibodies, or antigen targets.

Another advantageous construct is a multimeric protein in which the polypeptide fusion fragments contain:

in A, an antigen, in particular a vaccinating antigen or a therapeutic enzyme or a CD35 (or CR1) or an antibody, or any fragment thereof which possesses the ligand property of the whole molecule;

in B, an antibody or a fragment thereof which has retained its paratope;

Another advantageous recombinant multimeric proteins are those in which the polypeptide fusion fragments contains:

in A, a vaccinating immunogen, and in B, a CD4 or a derived molecule, provided that it retains the ligand property of the whole molecule.

In addition, the present invention is directed toward eukaryotic or prokaryotic cells which are transduced with one or more plasmids containing a heterologous nucleic acid sequence and encoding at least one polypeptide fusion molecule A and one polypeptide fusion molecule B.

The different cell lines which can be used for being transduced with plasmids are preferably eukaryotic cells which are capable of carrying out post-translational glycosylation; those which may be mentioned by way of example are yeasts or animal cell lines such as cells of the fibroblast type, such as BHK or CHO cells, or else lymphocyte cell lines such as immortalized lymphocytes.

According to different embodiments of the present invention, the cells can be:

cotransduced with two separate plasmids, or transduced with a plasmid encoding a first polypeptide and then supertransduced with the second plasmid encoding the second polypeptide, or result from the fusion of two cells, one of which has been transduced with the plasmid encoding the first polypeptide while the other has been transduced with a plasmid encoding the second polypeptide.

The cell fusions are carried out using standard methods, either by action of PEG (polyethylene glycol) or by action of Epstein-Barr virus, or using any other standard method for fusing two different eukaryotic cells.

More specifically, said cells can be transduced with the first plasmid, which is that which was deposited in the C.N.C.M. under No. I-1610 on 12 Jul. 1995, and with the second plasmid, which is that which was deposited in the C.N.C.M. under No. I-1611 on 12 Jul. 1995.

The present invention also relates to a process for preparing a multimeric protein according to the invention. This process is characterized in that it comprises at least the following steps:

transducing target cell lines with at least one plasmid containing a heterologous sequence encoding an A chain or a B chain, as defined above, expressing and isolating of the heterologous A or B chains, placing said polypeptides, in specific proportions, in an oxidizing medium, isolating the multimers.

Preferably, this preparation process is characterized in that the transduced cell lines have been either:

cotransduced with two plasmids carrying DNA sequences which respectively encode the A and B polypeptides, or transduced with a plasmid encoding a first polypeptide and then supertransduced with the second plasmid encoding the second polypeptide, or result from the fusion of two cells, one of which has been transduced with the plasmid encoding the first polypeptide while the other has been transduced with a plasmid encoding the second polypeptide.

Furthermore, the present invention relates to the use of a recombinant protein as previously defined in the production of a medicament and, more particularly, of a medicament which is intended for:

prevention of fetomaternal alloimmunization, or the therapy or prophylaxis of viral, bacterial or parasitic infections, the therapy of autoimmune diseases, in particular disseminated lupus erythematosus, or alloimmune diseases.

More generally, the present invention relates to the use of a recombinant protein as previously defined in the production of a medicament which makes it possible, depending on the functionality which is attributed to the ligands or the receptors, to effect an immunointervention, in particular in the opsonization or non-opsonization of target cells by means of activating, modulating or inhibiting complement.

The skilled person will know, in step with discovering the functionalities of certain proteins or of certain ligands or receptors, how to construct a recombinant multimeric protein according to the invention which is best suited for the sought-after effect.

Advantageously, the use of the multimeric protein according to the invention is characterized in that it enables complement to be sufficiently activated to induce opsonization of cells whose antigenic or epitopic sites are not naturally able to trigger such activation.

A pharmaceutical composition which is characterized in that it comprises, as the active principle, a recombinant multimeric protein as described above is also included within the scope of the present invention. Said pharmaceutical composition can enable the immunotherapy or the immunoprevention of different pathologies, in particular those which are linked to viral or bacterial infections or to autoimmune or alloimmune diseases.

A recombinant protein according to the invention can also be used in a diagnostic test which requires the intervention of at least two different ligands or receptors.

The feasibility of the multimer of very high molecular weight was verified in a multi-CR1 model (approx. 1.5 million daltons). This molecule is functional and inhibits complement activation in a model of complement-dependent, antibody-covered erythrocyte lysis at concentrations which are lower than those required for monomeric soluble CR1.

The feasibility of heterochimeras which combine different functions was then established using, on the one hand, anti-Rh(D) antibody, more specifically the variable Fv moiety of this antibody, and even more specifically the single-chain moiety of this variable moiety, termed scFv, which, in the present case, was linked to the CD35 or (CR1) molecule, which is able to inhibit or modulate complement activity; the other system employed is a heteromultimeric system of the CD4/antigen type.

BRIEF DESCRIPTION OF THE DRAWINGS

The examples which follow are in no way limiting and only serve to demonstrate the feasibility of the constructs of these recombinant heteromultimers for the purposes of immunointervention; the figures which illustrate the examples have the following meanings:

FIG. 3 depicts a plasmid vector which contains the sequence encoding multimeric CR1;

FIG. 4 depicts another plasmid vector, pCDM8, which encodes the same multimeric CR1;

In all these figures, the restriction enzymes enabling the heterologous sequence to be inserted are indicated by their standard nomenclature.

FIG. 9 depicts the result which is obtained with the multimeric scFv when agglutinating red blood corpuscles which either do or do not exhibit the rhesus antigen. The tube in A depicts the positive control, in which the O Rh+ red blood corpuscles are agglutinated by a native anti-R(h) monoclonal antibody; tube B depicts the negative control, in which O Rh− red blood corpuscles are not agglutinated by the multimeric anti-R(h) scFv antibodies; tube C depicts the assay in which O Rh+ red blood corpuscles and anti-Rh+ scFv are agglutinated; tube D is another negative control in which the O Rh− red blood corpuscles are mixed with a culture medium which lacks antibody.

Figure 10:
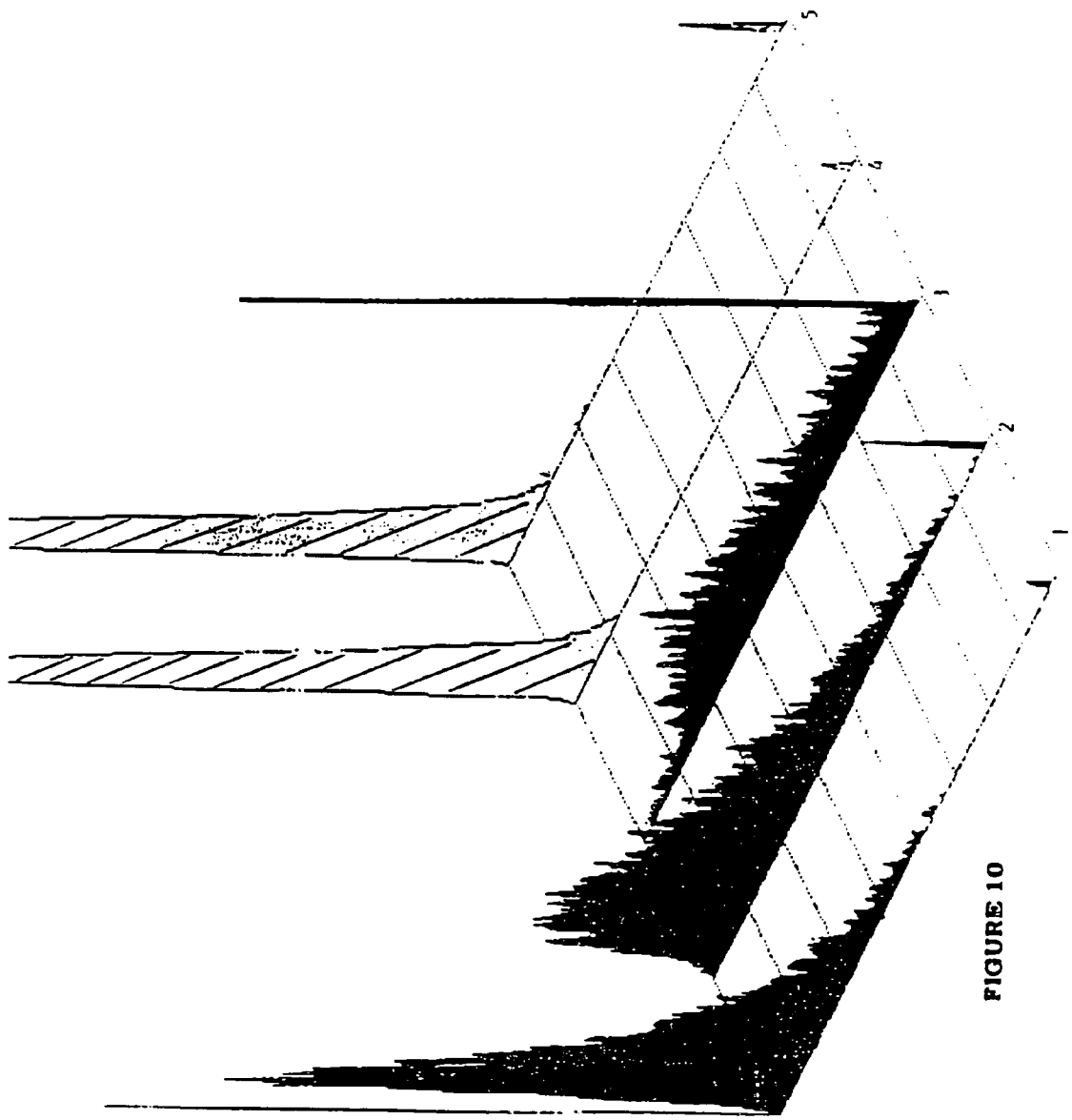

FIG. 10 depicts the profile which is obtained in flow cytometry after binding an anti-Rh(D) antibody-CR1 heterochimera to erythrocytes.

Five tracks are depicted, in which:

the first track depicts non-papainated O Rh+ red blood corpuscles having a CR1 density of 180 sites;

the second track depicts non-papainated O Rh+ red blood corpuscles having a CR1 density of 550 sites;

the third track depicts papainated O Rh+ red blood corpuscles which have lost their density of 180 CR1 sites; these erythrocytes, which have been reconstituted with respect to CR1 using the anti-Rh+ scFv/CR1 heterochimera, are expressing the supraphysiological density of 1200 CR1 sites per erythroctye;

tracks 4 and 5 depict controls, which are papainated O Rh+ red blood corpuscles in the case of track 4 and papainated O Rh− red blood corpuscles treated with the anti-Rh(D) scFv/CR1 heterochimera in the case of track 5.

DETAILED DESCRIPTION OF THE INVENTION

I—Construction of the CR1-C4BP Chains

The advantage of using CR1 in a multimeric construct according to the invention results from the studies carried out by the inventors on the physiological fate of CR1 in the normal subject. Thus, the inventors have been able to determine the parameters of a physiological catabolism of erythrocytic CR1 and its relationships with the genetic polymorphism of erythrocytic CR1 density. They have also been able to clarify the catabolism of erythrocytic CR1 in lupus patients, that is patients who are suffering from disseminated lupus erythematosus. The distribution among lupus patients and normal subjects of the different genotypes of length polymorphism and CR1 C3b/C4b-binding site number polymorphism has also been studied. Recombinant CR1 molecules which make it possible to change the erythrocytic CR1 density in order to restore the physiological state of the erythrocytes or to produce "armed" erythrocytes having "supraphysiological" densities of CR1 have then been prepared. The potential of soluble CR1 was demonstrated in different models, in particular models of experimental myocardial ischemia and of Arthus phenomenon. A molecule of multimeric soluble CR1 is produced and its anti-inflammatory power, its plasma life span and its distribution space are studied in the animal. Reduced monomers are coupled chemically to erythrocytes by means of their free SH group. In this way, erythrocytes are armed with supraphysiological densities of CR1, with the CR1 being presented in a functional manner, and the ability of the erythrocytes to bind artificial C3b-opsonized Hbs antigen/anti-HBs antibody immune complexes is then studied.

The results which were obtained with an anti-Rh(D) antibody are shown in Example I below.

Figure 8:
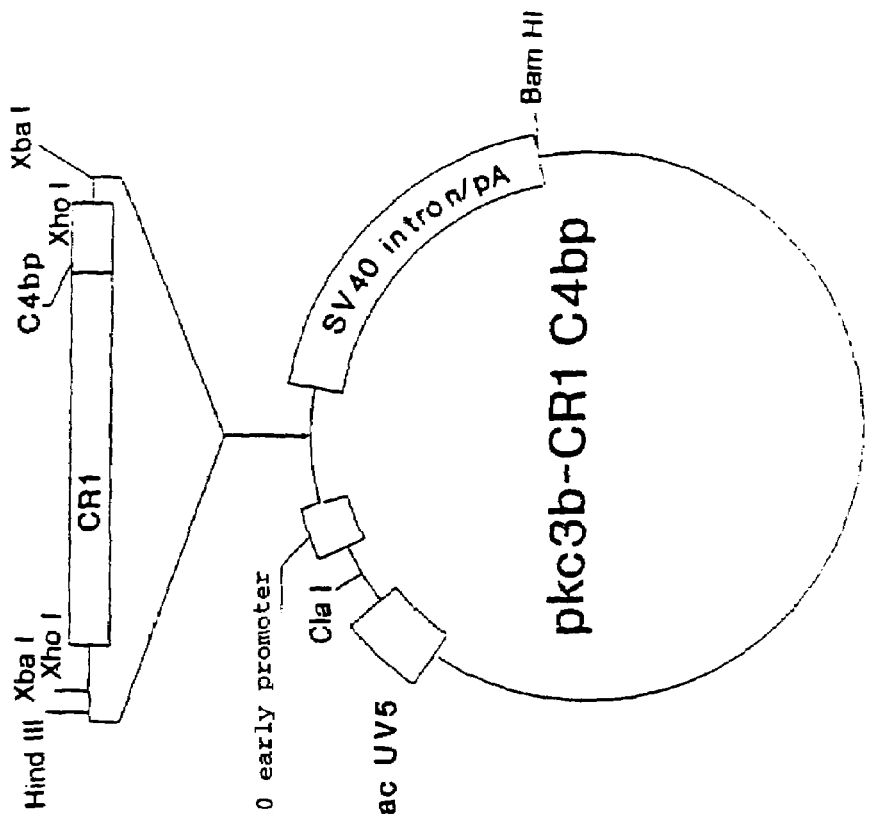
FIG. 8 depicts a plasmid vector of the pKC3B type which contains the sequence encoding multimeric CR1.

The constructs which were used for carrying out the C4BP-CR1 transduction are depicted in FIGS. 3, 4 and 8, in plasmids pMAMneo, pCDM8 and pKC3b.

a) Construction of pMAMneo CR1-C4BP:

The complementary DNA encoding CR1 had been inserted into the Xho I and Not I sites in plasmid pCDM8 (due to the kindness of T. J. Bartow, D. T. Fearon and W. Wong, John Hopkins Hospital, Baltimore, U.S.A.). The sequence encoding the extramembrane moiety of CR1 is extracted by digesting this plasmid with the restriction enzymes Xho I and Bal I in a moiety of C4BP is amplified using the primers (SEQ ID NOS 1 and 2 respectively) 5'-GAGACCCCCGAAGGCTGTGA-3', and 5'-CTCGAGT-TATAGTTCTTTATCCCAAGTGG-3', with this second primer containing a stop codon and a Xho I restriction site.

The sequences encoding the C-terminal moiety of C4BP and the extramembrane moiety of CR1 are inserted into pMAMNeo (Clontech, Palo Alto, USA) at the Xho I site (FIG. 3) CR1-C4BP by digestion with Xho I, and inserted into plasmid pCDM8 (Invitrogen, San Diego, USA).

b) Construction of pCDM8 CR1-C4BP:

The sequence encoding the CR1-C4BP fusion protein was extracted from pMAMNeo CR1-C4BP by digestion with Xho I and inserted into plasmid pCDM8 (Invitrogen, San Diego, USA) (FIG. 4).

c) Construction of pKC3b CR1-C4BP:

The sequence encoding the CR1-C4BP fusion protein was extracted from pMAMNeo CR1-C4BP by digestion with Xho I, and inserted into plasmid pKC3b (FIG. 8).

II—Construction of the Recombinant Multimer:

A C-terminal fragment of the α chain of C4BP was recopied from genomic DNA by means of PCR. It is found in one single exon. The minimum size is beyond the second cysteine proceeding from the C-terminal end, with the optimum size being a few amino acids beyond that, creating a spacer of from 5 to 10 amino acids, that is 58 AA in all.

The maximum size selected is of 6 SCRs, in order to avoid the C3b-C4b-binding site. This maximum fragment is synthesized from a cDNA prepared from C4BP mRNA, since the fragment is made up of several exons. The optimum fragment of the C-terminal moiety of C4BP is recopied once again by means of PCR using primers which are provided at their ends with arms containing enzyme restriction sites which are adequate for inserting the fragment into a given vector which already contains the gene for the protein which it is desired to multimerize. An enzyme site close to the C-terminal moiety of this protein, or which is located in its extramembrane moiety, is selected which enables the multimerizing fragment to be inserted in the 3' position.

The 3' end of the multimerizing fragment is linked either to a site in the vector or to a site beyond in the gene for the protein of interest. That part of the gene for the protein of interest which is located 3' of the multimerizing fragment is in any case no longer translated since the multimerizing fragment contains a stop codon.

It is therefore in this way possible to modify an expression vector containing the gene for a given protein very readily by simply inserting the fragment without any other alteration.

The vectors pCDM8, ST4 and pMAMneo have been used for the different examples of applying the multimeric system according to the invention.

The skilled person will always know how to find vectors which currently exist or which could be developed and which are/could be able to exhibit the optimum efficacy for transducing the fusion protein into cells and expressing it.

APPLICATION EXAMPLE NO. 1

Prevention of Anti-Rh(D) Alloimmunization.

Heteromultimeric molecules combining erythrocytic functions and CR1 are produced within the context of preventing anti-Rh(D) alloimmunization. They will make it possible to bind CR1 readily to erythrocytes, thereby ensuring the achievement of CR1 densities which can be fully controlled.

The antibody molecule used to generate the anti-Rh(D) scFv was produced and sequenced in Philippe ROUGER's laboratory at the Institut National de Transfusion Sanguine [National Blood Transfusion Institute] (INTS) (9).

Construction of Vectors which Comprise the Sequence Encoding the Anti-Rh(D) scFv and the Terminal Moiety of the α Chain of C4BP.

An epitope site of an anti-rhesus antibody was first of all reduced down to a structure of the scFv (denoting single-chain Fv) type for expression in *E. Coli* by means of transfecting with a phage vector.

Constructs of the scFv type are antibody fragments which represent the variable moiety of the antibody and only contain one single chain. This technique has been described by G. WINTER (10). The sequence encoding this scFv was then transferred into an expression vector after adding the multimerizing system.

Figure 6:
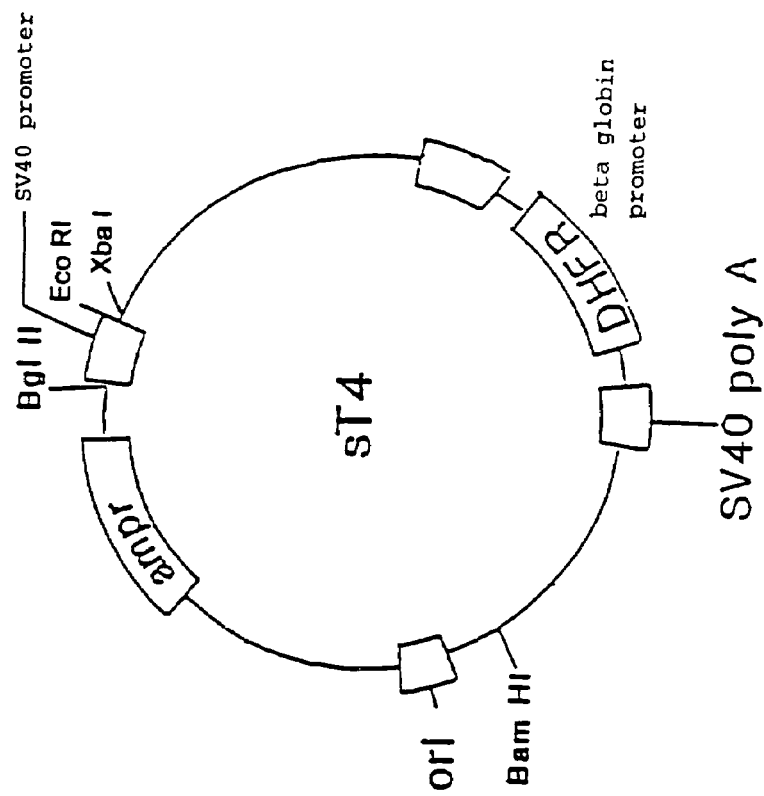
FIG. 6 depicts another plasmid vector, pST4, which contains the same sequence encoding the scFv of anti-Rh(D) antibody.
Figure 5:
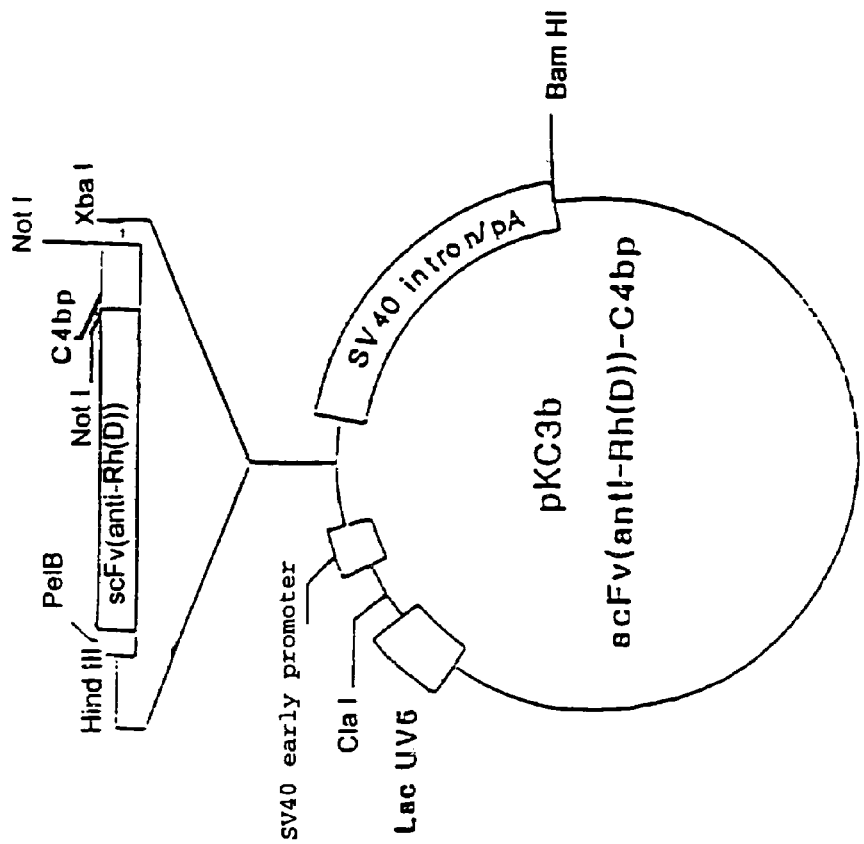
FIG. 5 depicts a plasmid vector which contains the sequence encoding the scFv of multimeric anti-Rh(D) antibody.
Figure 7:
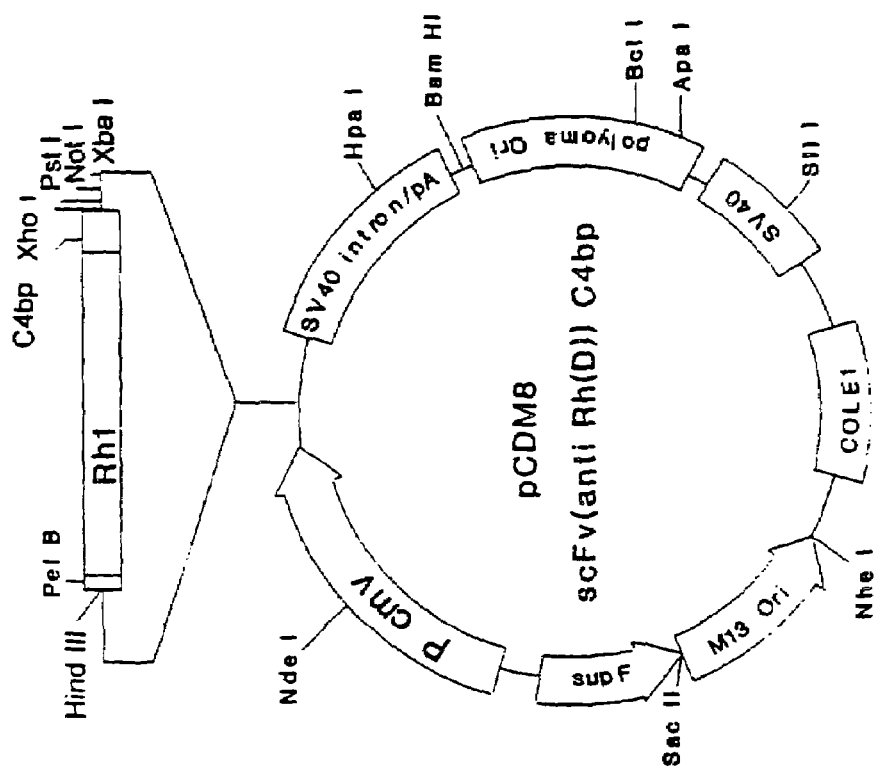
FIG. 7 depicts a third plasmid vector which contains this same sequence encoding the scFv of anti-Rh(D) antibody.
Figure 8:

We have described above the construction of expression vectors which carry the sequence encoding the scFv of the anti-Rh(D) antibody and which are depicted in FIGS. 6 and 7.

The C-terminal moiety of C4BP was amplified using the primers (SEQ ID NOS 3 and 4, respectively) 5'-GCGGC-CGCAGAGACCCCCGAAGGCTGTG-31, which contains a Not I restriction site, and 5'-CCACTTTGGATAAA-GAACTATAA-3', which contains a Xho I restriction site.

This fragment was inserted into the Not I site 3' of the anti-Rh(D) scFv gene. This sequence was then inserted into plasmid pCDM8 and inserted between the Hind III and Xho I sites of pKC3b. This construct is depicted in FIG. 5.

FIG. 5 depicts another construct of anti-Rh(D) scFv-C4BP in plasmid pKC 3B.

The plasmids are then used to transduce animal cells, in particular CHO $DHFR^-$ cells.

The CHO-$DHFR^-$ cells (American Type Culture Collection, Rockville, USA) were transfected using the calcium phosphate technique (Calcium phosphate transfection kit, 5 prime 3 prime Inc., Boulder, U.S.A.). These cells are cultured in HAM medium lacking in Hypoxanthine and Thymidine (Biochrom, Vindelle, France) containing 10% dialysed calf serum (FCS, GIBCO BRL, Paisley, Scotland) and 1% glutamine (Sigma, St. Louis, USA).

The functionality of the reconstituted multimeric proteins, which were either C4BP-scFv or C4BP-Rh(D)/CR1, was studied.

Success was achieved in producing functional multimeric scFv, as was demonstrated (i) by biosynthetic labeling and immunoprecipitation followed by SDS PAGE analysis, (ii) by detecting erythrocyte-bound multi anti-Rh(D) scFvs by flow cytometry, (iii) by the ability of multi anti-Rh(D) scFv chimeras to agglutinate papainated red blood corpuscles at weak ionic strength, (iiii) by analyzing molecular interactions using an instrument for detecting evanescent waves (IASys FISONS), with the instrument verifying the binding of the multimeric anti-Rh(D) anti scFv chimera to erythrocytes.

Subsequently, the feasibility of creating heteromultimers which combine different functions was established by preparing an anti-rhesus D antibody/CR1 chimera. Its ability to function was demonstrated by flow cytometry. The results which were obtained by flow cytometry are depicted in FIG. 10. It is clear from this figure that, if tracks 3 and 5, in which the red blood corpuscles are Rh+ and Rh−, respectively, are compared, it is observed that only the red blood corpuscles which possess the surface antigen are agglutinated. This figure also shows that this agglutination is not due to the effect of the papain since the papainated Rh+ red blood corpuscles are not agglutinated by CR1.

It was therefore possible to bind a supraphysiological density of CR1 molecules on erythrocytes which had been previously papainated, and therefore depleted of CR1, by binding a mixed multimeric anti-Rh(D) antibody/CR1 chimera to the rhesus D molecules.

APPLICATION EXAMPLE NO. 2

Extracellular Destruction of HIV

Even though the humoral immune response is unable to eradicate the HIV virus, it is nevertheless effective against a large number of infectious agents against which neutralizing antibodies are regularly produced by vaccinated subjects.

Natural antibodies can confer protection against a large number of bacterial or viral infectious agents which infect other species.

Certain antigenic motifs have been characterized as targets for this type of antibody in connection with their role in the peracute vascular rejection of xenogeneic transplants.

The potentially unfavorable role of the humoral immune response and of complement activation with regard to infection with HIV virus has been demonstrated.

Under certain circumstances, opsonization of the virions can facilitate ingestion by macrophages or binding of the virions to lymphocytes by way of cell receptors for complement or the IgG Fc fragment. On the other hand, the HIV virus, as an enveloped virus, is extremely sensitive to the lytic action of complement when the latter has been sufficiently activated to initiate its final lytic path and binding of its membrane attack complex. Xenogenic retroviruses are destroyed extremely efficiently by normal human serum, due to the existence of natural antibodies, by way of activating complement. In the 1970s, this phenomenon had even led to the conclusion that the human species was naturally immune to retroviruses.

The sought-after aim is to reroute a lytic humoral immune response toward HIV virions, with attachment to the virions being effected by the CD4 component of a recombinant heteromultimeric protein. For this, the inventors have taken into account the fact that while the HIV virus exhibits a very high degree of variability, this variability is nevertheless limited by the necessity of having constantly to preserve an ability to bind to CD4, which ability is required for the virus to penetrate the cell and is essential for the virus. In a reciprocal manner, the CD4 molecule is able to bind to all HIV virions, in contrast to a large number of neutralizing antibodies, which have a spectrum of efficacy which is restricted to a small number of subtypes. The soluble CD4 molecule inhibits cell infection by HIV. However, the concentrations which are required for it to have this effect, particularly for neutralizing wild-type isolates, render its clinical use impracticable. Various attempts have been made to improve its half-life and its avidity, and/or supply an Fc gamma function which effects cell binding or complement activation using constructs of the bivalent or tetravalent CD4/IgG type.

The inventors have developed a heptameric multivalent CD4 molecule using a multimerizing C4BP system whose biological efficacy in vitro was demonstrated by inhibiting infection of susceptible cells by HIV at inhibitory concentrations which are common for monomeric soluble CD4.

In the present example, rather than inhibiting cell penetration by the virus, the inventors have sought to destroy the virus extracellularly using soluble molecules which are able, on the one hand, to bind to the virion and, on the other, to supply an antigenic effector function which elicits destruction of the virus by means of an antibody response which depends on complement which pre-exists in the individual patient. This response is directed against an antigen which has nothing to do with the HIV but in relation to which the immune system has nevertheless been demonstrated to exhibit neutralizing and lytic efficacy. In other words, since the HIV virus has the ability to “disguise” itself, to “hide” itself or to “raise decoys”, the inventors have sought to embellish the virus with targets which the immune system of the individual patient knows how to identify and deal with efficiently.

In order to do this, two plasmid constructs were made which respectively carry CD4 or the fragment of CD4 which carries the “ligand” fraction and an antigen.

a) Construction of Vector ST4 CD4-C4BP

The last 183 nucleotides of the sequence encoding C4BP were amplified by means of PCR, on genomic DNA, using the following primers (SEQ ID NOS 1 and 5, respectively): 5'-GAGACCCCCGAAGGCTGTGTGA-3, and 5'-ATTTCTAGAGAGTTATAGTTCTTTATC-CAAAGTGGA-3', with this latter primer containing a stop codon and a restriction site for Xba I. This PCR fragment was linked at its 5' end to the following double-stranded synthetic oligonucleotide sequence (SEQ ID NO:6); 5'CCGGGACAGGTCCTGCTGGAATCCAA-CATCAAGGTTCTGCCCACAG-3'. This fragment encoding the C-terminal end of the extramembrane moiety of CD4 and having an Ava I site at its 5' end.

Figures 1, 2:
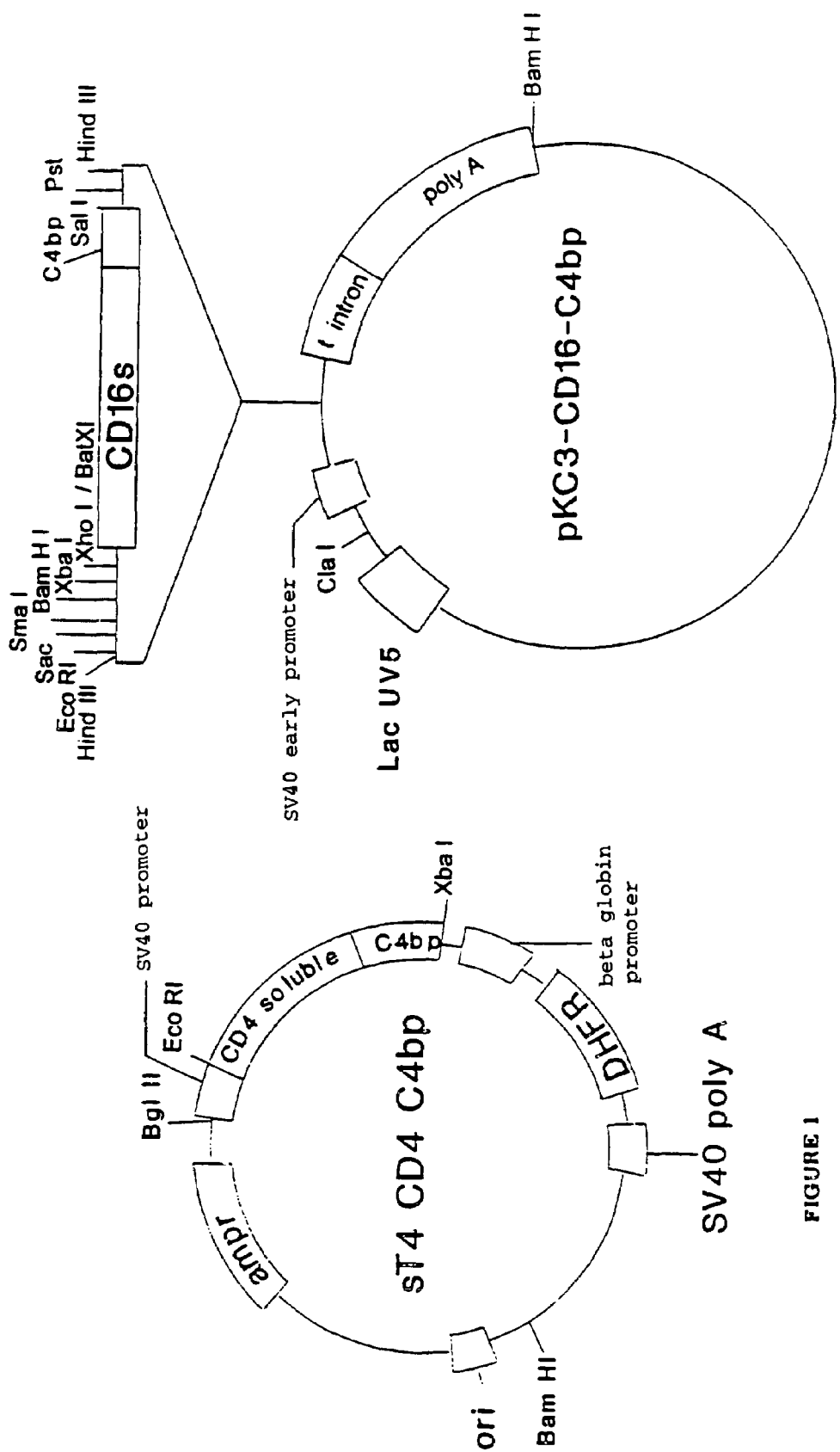
FIG. 1 depicts an expression vector which consists of a plasmid which contains the sequence encoding CD4 and which is termed sT4CD4-C4BP.
FIG. 2 depicts a plasmid vector which contains the sequence encoding multimeric CD16.

This sequence was inserted into the Ava I and Xba I sites in plasmid sT4 CD4, containing the construct encoding soluble CD4, and this construct is depicted in FIG. 1.

b) Construction of C4BP-Antigen Fusion Molecules

It is firstly a matter of trying to determine which parameters direct the anti-gp120 antibody response of infected subjects to complement activation up to the C3 amplification loop, resulting in opsonization which is relatively advantageous for the individual patient, without, for all that, being accompanied by activation of the final common pathway which would result in lysis of the virion. The role of surface molecules which inhibit activation of complement and which the virion has taken from the cell surface has been demonstrated. The shedding of envelope particles when antibody is being bound also militates against terminal activation of complement. Activation of the final common complement pathway requires the C3 to have a density which is critical for activation in order to initiate C5 conversion. This conversion is not brought about by IgG being bound to gp120 epitopes which are too distant from each other.

The use of the constructs of the invention to supply a "cluster" of antigens for each binding site on the virion thus makes it possible to trigger adequate local activation of complement.

Various categories of antigen have been considered: vaccinating antigens, bacterial antigens against which humans are universally immunized, and xenogenic antigens which are the targets of natural antibodies.

vaccinating antigens which exist in the form of cloned genes and which encode a protein which can be expressed in eukaryotic cells (Hbs antigen, tetanus toxoid, etc.), bacterial antigens to which there exists strong immunity in humans (*Escherichia coli, Klebsiella, Shigella flagellin* or *Salmonella* antigen), molecules which possess protein sequences which accept xenogenic glycosylations may also be envisaged after they have been produced by animal cells which possess strong glycosyl transferase activities which will attach to the proteins carbohydrates which are the targets of natural antibodies and which are known to react strongly in xenotransplants (for example: the alpha-galactosyl group, which is an impediment to xenogeneic pig/man transplants).

These miniantibodies will be used as agents for binding heterochimeras to erythrocytes, of which chimeras they only represent one valency of the C4BP β type, which valency is linked to a multimeric antigenic molecule of the heptameric C4BP α type. The most effective antigenic system will therefore be selected in a readily quantifiable screening test. It will then be transferred into a recombinant CD4/antigen target chimera whose different CD4/antigen ratios (1CD4/7 antigens or nCD4/M antigens) will be tested in an in-vitro model of the inhibition of viral infection.

These miniantibodies will be used as agents for binding heterochimeras to erythrocytes, of which chimeras they only represent one valency of the C4BP beta type, which valency is linked to a multimeric antigenic molecule of the heptameric C4BP alpha type. The most effective antigenic system will therefore be selected in a readily quantifiable screening test. It will then be transferred into a recombinant CD4/antigen target chimera whose different CD4/antigen ratios (1CD4/7 antigens or nCD4/M antigens) will be tested in an in-vitro model of the inhibition of viral infection.

The most interesting target antigens were inserted into heteromultimeric constructs containing CD4 and tested for their ability to enable HIV virions to be destroyed in the presence of human serum and complement, with residual infectivity being evaluated in an in-vitro test of the inhibition of cell infection.

Materials and Methods:

In addition to the abovementioned constructs, the techniques employed for transfecting and culturing cells were as follows:

Transfection:

DHFR$^-$ CHO cells (American Type Culture Collection, Rockville, USA) were transfected using the calcium phosphate technique (Calcium phosphate transfection kit, 5 prime 3 prime Inc., Boulder, U.S.A.).

Cell Culture:

The cells are cultured in HAM medium lacking Hypoxanthine and Thymidine (Biochrom, Vindelle, France) but which contains 10% dialyzed calf serum (FCS GIBCO BRL, Paisley, Scotland) and 1% glutamine (Sigma, St. Louis, USA).

The cells which have been transfected with pMAMNeo are selected on the basis of their ability to resist neomycin (G418, 0.7 microg/ml) (Sigma). Dexamethasone (0.8 microg/ml) is used to induce the production of mCR1 in the cells which are transfected with the pMAMneo CR1-C4BP.

In their experiments, the inventors used an appliance for culturing cells continuously in hollow fibers in order to produce recombinant proteins on the scale of a few milligrams, or a few tens of milligrams, of recombinant proteins. Most of the experiments can be carried out using crude or concentrated culture supernatants. Small-scale purified preparations have also been prepared.

The oligonucleotide syntheses which were employed for constructing the vectors were carried out in order to fit the C-terminal C4BP fragment to each construct. The nucleotide sequences were also determined on an automated fluorescence sequencer in order to check the constructs.

Comments

The multimeric proteins of the invention, and their use in producing a medicament for prophylactic or therapeutic purposes, or their use as a diagnostic or research tool, are very powerful.

Using them can be an efficient tool for analyzing physiological mechanisms in the immune response as well as for understanding the physiopathology of certain disorders of the immune system.

These molecules should make it possible to intervene in the immune system in a more sophisticated manner, thereby opening up the possibility of being better able to study large numbers of physiopathological mechanisms in vitro. In certain cases, this immunointervention will open up the route to manipulating the immune system in vivo for therapeutic purposes. The molecules are, therefore, at one and the same time tools for carrying out clinical physiopathological research and in vitro experimental research and also therapeutic tools for use in vivo.

BIBLIOGRAPHY

1. Matsuguchi T., Okamura S., Aso T., Niho Y., Molecular cloning of the cDNA coding for PRP: identity of PRP as C4BP. Biochem Biophys Res Commun 1989; 1: 139–44.
2. Scharfstein J., Ferreira A., Gigli I., Nussenzweig V., Human C4-binding protein. I. Isolation and characterization. J. exp Med 1978; 148: 207–22.
3. Fujita T., Gigli I., Nussenzweig V., Human C4-binding protein II. Role in proteolysis of C4b by C3b-inactivator. J. Exp Med 1978; 148: 1044–51.
4. Chung L. P., Bentley D. R., Reid K. B. M., Molecular cloning and characterization of the cDNA coding for C4b-binding protein, a regulatory protein of the classical pathway of the human comlement system. Biochemistry 1985: 230: 133–41.
5. Monte G. Thrombosis and Haemostasis-69(1)86(1993).
6. Hillarp A., (1990) PNAS vol. 87 pp. 1183–1187.
7. Hillarp A., (1991) Scand. J. Chin. Lab. Invest. Fi, Suppl. 204: 57–69.
8. Fanger M. W., Immunomethods 1994-p. 72 to 81 "Production and use of anti-FcR bi-specific antibodies".
9. Goossens D., Champomier F., Rouger Ph. and Salmon Ch., Human monoclonal antibodies against blood group antigens: preparation of a series of stable EBV Immortalized B clones producing high levels of antibody of different isotypes and specifites.
   J. of immonological methods., 101, 193, 1987.
10. Winter G., Nature 1990-348-p. 552–554. M. Cafferty J., Griffiths A., Winter G., Chiswell. "Phage antibodies filamentous phase displaying antibody variable domains".

The invention claimed is:

1. A recombinant multimeric protein, comprising
   a) a polypeptide fusion monomer A, which consists of a C-terminal fragment of the α chain of C4BP containing one or two cysteine residues, wherein the C-terminal fragment is contained within the amino acid sequence represented by SEQ ID NO:7, and a polypeptide fragment which is heterologous in relation to said α chain, and
   b) a polypeptide fusion monomer B, which consists of a C-terminal fragment of the β chain of C4BP containing one or two cysteine residues, wherein the C-terminal fragment is contained within the amino acid sequence represented by SEQ ID NO:8, and a polypeptide fragment which is heterologous in relation to the β chain,
   monomer A and monomer B being linked to each other by a disulfide bridge between a cysteine of the α chain C terminal fragment and a cysteine of the β chain C-terminal fragment to form said multimeric protein.

2. A recombinant multimeric protein according to claim 1, wherein the ratio of the number of monomers A/B varies between 7/1 and 5/3.

3. A recombinant multimeric protein according to claim 1, wherein the heterologous fragments in monomer A and in monomer B are ligands of the immune system, selected from group consisting of CD lymphocyte surface proteins, antibodies, antibody fragments, antigens and antigen fragments.

4. A recombinant multimeric protein according to claim 3, wherein the lymphocyte surface proteins are selected from the group consisting of CD4, CD8, CD16, CD35, CR1 and combinations thereof.

5. A recombinant multimeric protein according to claim 3, wherein the antibodies or antibody fragments are specific for anti-Rh (D).

6. A recombinant multimeric protein according to claim 3, wherein the antigens are vaccinating antigens.

7. A recombinant multimeric protein according to claim 1, wherein the heterologous fragment in monomer A is a therapeutic enzyme.

8. A recombinant multimeric protein according to claim 1, wherein the polypeptide fusion monomer A comprises CD4 or a fragment thereof, and monomer B comprises the scFv of an antibody.

9. A recombinant multimeric protein according to claim 1, wherein the polypeptide fusion monomer A comprises
  a ligand selected from the group consisting of an antigen, a therapeutic enzyme, a CD35, CR1, an antibody and any fragment thereof which possesses the ligand property of the whole ligand molecule, and monomer B comprises
  an antibody or a fragment thereof which has retained its epitope.

10. A recombinant multimeric protein according to claim 1, wherein the polypeptide fusion monomer A comprises a vaccinating immunogen, and monomer B comprises a CD4 or a fragment thereof that retains the ligand property of the whole molecule.

11. An isolated host cell into which has been introduced a heterologous nucleic acid which encodes a recombinant multimeric protein, comprising
  a) a polypeptide fusion monomer A, which consists of a C-terminal fragment of the α chain of C4BP containing one or two cysteine residues, wherein the C-terminal fragment is contained within the amino acid sequence represented by SEQ ID NO:7, and a polypeptide fragment which is heterologous in relation to said α chain, and
  b) a polypeptide fusion monomer B, which consists of a C-terminal fragment of the β chain of C4BP containing one or two cysteine residues, wherein the C-terminal fragment is contained within the amino acid sequence represented by SEQ ID NO:8, and a polypeptide fragment which is heterologous in relation to the β chain,
  monomer A and monomer B being linked to each other by a disulfide bridge between a cysteine of the α chain C terminal fragment and a cysteine of the β chain C-terminal fragment to form said multimeric protein.

12. A host cell according to claim 11, wherein the heterologous nucleic acid sequences have been introduced by either
  introducing two separate plasmids comprising the two heterologous nucleic acid sequences, or
  transducing with a first plasmid encoding one of molecule A and molecule B and then transducing again with a second plasmid encoding the other of molecule A and B, or
  fusing two cells, one of which has been transduced with a plasmid encoding one of molecule A and molecule B while the other has been transduced with a plasmid encoding the other of molecule A and B.

13. A host cell according to claim 11, wherein the heterologous nucleic acid sequences are contained in first and second plasmids, of which the first plasmid is that which was deposited in the C.N.C.M. under No. I-1610 on 12 Jul. 1995, and the second plasmid is that which was deposited in the C.N.C.M. under No. I-1611 on 12 Jul. 1995.

14. A method for preparing a multimeric protein as defined in claim 1, the method comprising the following steps:
  transducing at least two target cell lines with at least one plasmid each, each of which plasmids contains a heterologous sequence which respectively encodes a molecule A or a molecule B according to claim 1,
  expressing and isolating the heterologous molecule A and molecule B from the at least two target cell lines,
  placing said molecules, in molecular ratio leading to the predetermination of the expected ratio of the different moieties of the heterologous molecules, in an oxidizing medium to form multimers and,
  isolating the multimers.

15. The method according to claim 14, wherein the transduced lines have been either:
  cotransduced with two plasmids carrying DNA sequences which respectively encode the A and B molecules, or
  transduced with a first plasmid encoding one of molecule A and molecule B and then transduced again with a second plasmid encoding the other of molecule A and molecule B, or
  fused from two cells which have, respectively, been transduced with a plasmid carrying a DNA sequence which encodes molecule A and with a plasmid carrying a DNA sequence which encodes molecule B.

16. A composition comprising a recombinant multimeric protein according to claim 1.

17. A diagnostic test kit comprising a recombinant multimeric protein according to claim 1 and able to detect the presence of at least two different ligands with affinity for the heterologous polypeptide fragment of molecule A and the heterologous polypeptide fragment of molecule B, respectively.

18. A recombinant multimeric protein according to claim 1, wherein the C-terminal fragment of the α chain comprises SEQ ID NO 9, and the C-terminal fragment of the β chain comprises SEQ ID NO 10.

19. A recombinant multimeric protein according to claim 1, wherein the C-terminal fragment of the α chain and the C-terminal fragment of the β chain each include two cysteine residues.

20. A recombinant multimeric protein according to claim 19, wherein the cysteine residues of the C-terminal of the α chain are located at positions 498 and 510 of SEQ ID NO:7 and the cysteine residues of the C-terminal of the β chain are located at positions 510 and 549 of SEQ ID NO 8.

21. A recombinant multimeric protein according to claim 1, comprising at least one each of monomer A and monomer B, and at least seven monomers A and B in all.

22. A recombinant multimeric protein, comprising
a.) a polypeptide fusion monomer A, which consists of a cysteine-containing C-terminal fragment of the α chain of C4BP containing one or two cysteine residues, wherein the C-terminal fragment is contained within the amino acid sequence represented by SEQ ID NO 7, and a polypeptide fragment, which is heterologous in relation to said α chain and is a ligand of the immune system,
b.) a polypeptide fusion monomer B, which consists of a cysteine-containing C-terminal fragment of the β chain of C4BP containing one or two cysteine residues, wherein the C-terminal fragment is contained within the amino acid sequence represented by SEQ ID NO 8, and a polypeptide fragment which is heterologous in relation to the β chain and is a ligand of the immune system,
monomer A and monomer B being linked to each other by a disulfide bridge between a cysteine of the α chain C terminal fragment and a cysteine of the β chain C-terminal fragment to form said multimeric protein.

23. A recombinant multimeric protein, comprising
a.) a polypeptide fusion monomer A, which consists of a cysteine-containing C-terminal fragment of the α chain of C4BP containing one or two cysteine residues, wherein the C-terminal fragment is contained within the amino acid sequence represented by SEQ ID NO 7, and a polypeptide fragment, which is heterologous in relation to said α chain and is a ligand of the immune system,
b.) a polypeptide fusion monomer B, which consists of a cysteine-containing C-terminal fragment of the β chain of C4BP containing one or two cysteine residues, wherein the C-terminal fragment is contained within the amino acid sequence represented by in SEQ ID NO 8, and a polypeptide fragment which is heterologous in relation to the β chain and is a ligand of the immune system,
monomer A and monomer B being linked to each other by a disulfide bridge between a cysteine of the α chain C terminal fragment and a cysteine of the β chain C-terminal fragment to form said multimeric protein, wherein said recombinant multimeric protein activates complement to induce opsonization of cells.

24. A recombinant multimeric protein, comprising
a.) a polypeptide fusion monomer A, which consists of a cysteine-containing C-terminal fragment of the α chain of C4BP containing one or two cysteine residues, wherein the C-terminal fragment is contained within the amino acid sequence represented by SEQ ID NO 7, and a polypeptide fragment, which is heterologous in relation to said α chain and is a ligand of the immune system,
b.) a polypeptide fusion monomer B, which consists of a cysteine-containing C-terminal fragment of the β chain of C4BP containing one or two cysteine residues, wherein the C-terminal fragment is contained within the amino acid sequence represented by SEQ ID NO 8, and a polypeptide fragment which is heterologous in relation to the β chain and is a ligand of the immune system,
monomer A and monomer B being linked to each other by a disulfide bridge between a cysteine of the α chain C terminal fragment and a cysteine of the β chain C-terminal fragment to form said multimeric protein, wherein said recombinant multimeric protein activates, modulates or inhibits complement.

* * * * *